(12) United States Patent
Bell et al.

(10) Patent No.: US 7,686,792 B2
(45) Date of Patent: Mar. 30, 2010

(54) MODULAR ABSORBENT ARTICLE WITH OVERLAPPING PORTIONS

(75) Inventors: Elizabeth Ellen Bell, Appleton, WI (US); Emily Jean Baum, Appleton, WI (US); Carmen Judith Dietz, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 985 days.

(21) Appl. No.: 10/458,571

(22) Filed: Jun. 9, 2003

(65) Prior Publication Data

US 2004/0249356 A1    Dec. 9, 2004

(51) Int. Cl.
*A61F 13/15* (2006.01)
*A61F 13/20* (2006.01)

(52) U.S. Cl. .............. 604/385.16; 604/385.01; 604/385.03; 604/385.11; 604/385.13; 604/385.14

(58) Field of Classification Search ........... 604/385.16, 604/358, 380, 385.01, 385.23, 385.19, 387, 604/385.03, 385.11, 385.13, 385.14, 385.15; 428/57–58, 137
See application file for complete search history.

(56) References Cited

U.S. PATENT DOCUMENTS

| | | | | |
|---|---|---|---|---|
| 4,315,507 A | * | 2/1982 | Whitehead et al. | 604/366 |
| 4,505,704 A | | 3/1985 | Roeder | |
| 4,536,181 A | * | 8/1985 | Cook | 604/387 |
| 4,579,556 A | | 4/1986 | McFarland | |
| 4,597,759 A | * | 7/1986 | Johnson | 604/385.16 |
| 5,683,373 A | * | 11/1997 | Darby | 604/385.01 |
| 5,704,929 A | | 1/1998 | Bien | |
| 5,704,932 A | | 1/1998 | Hibbard | |
| 6,254,582 B1 | | 7/2001 | O'Donnell et al. | |
| 6,277,105 B1 | | 8/2001 | Rynish | |
| 6,280,427 B1 | * | 8/2001 | Maggiulli | 604/385.01 |
| 6,296,628 B1 | * | 10/2001 | Mizutani | 604/387 |
| 6,524,290 B2 | * | 2/2003 | Motta et al. | 604/385.01 |

(Continued)

FOREIGN PATENT DOCUMENTS

EP    0 930 053 A1    7/1999

(Continued)

*Primary Examiner*—Leslie R. Deak
*Assistant Examiner*—Adam Marcetich
(74) *Attorney, Agent, or Firm*—Ralph H. Dean, Jr.; Sebastian C. Pugliese, III; Randall W. Fieldhack

(57) ABSTRACT

An absorbent article (20) includes a first pad section (26), and a smaller second pad section (28) which is operatively joined to the first pad section. The first pad section (26) includes a first body-side cover (30), a first backsheet (32), a first absorbent body (34) located between the first cover and the first backsheet, and a first garment-attachment mechanism (36) located on a garment-side surface of the first backsheet (32). The second pad section (28) includes a second body-side cover (38), a second backsheet (40), a second absorbent body (42) located between the second cover and the second backsheet, and a second garment-attachment mechanism (44) located on the garment-side surface of the second backsheet (40). In a desired arrangement, the first pad section (26) can overlap at least a portion of the second pad section (28), and at least a portion of the first garment-attachment mechanism (36) can operatively attach the first pad section (26) to the second pad section (28).

23 Claims, 4 Drawing Sheets

U.S. PATENT DOCUMENTS

| | | | |
|---|---|---|---|
| 6,689,114 B2 * | 2/2004 | Bouchard et al. | 604/385.14 |
| 2002/0077614 A1 * | 6/2002 | Molas et al. | 604/385.01 |
| 2002/0143311 A1 | 10/2002 | Brisebois | |
| 2002/0177832 A1 * | 11/2002 | Fernandez-Kleinlein et al. | 604/385.01 |
| 2002/0193766 A1 | 12/2002 | Gell et al. | |
| 2003/0088226 A1 * | 5/2003 | Takagi et al. | 604/385.16 |
| 2003/0125694 A1 * | 7/2003 | Motta et al. | 604/385.04 |

FOREIGN PATENT DOCUMENTS

| | | |
|---|---|---|
| EP | 1 005 307 B1 | 1/2002 |
| EP | 1 214 920 A2 | 6/2002 |
| EP | 1 245 209 A2 | 10/2002 |
| WO | WO 95/29655 A1 | 11/1995 |
| WO | WO 9529655 A1 * | 11/1995 |
| WO | WO 02/47596 A1 | 6/2002 |
| WO | WO 02/054999 A1 | 7/2002 |

* cited by examiner

MODULAR ABSORBENT ARTICLE WITH OVERLAPPING PORTIONS

FIELD OF THE INVENTION

The present invention relates to an absorbent article. More particularly, the present invention pertains to modular absorbent system for a feminine care article, such as an absorbent feminine care pad.

BACKGROUND OF THE INVENTION

Absorbent products intended to absorb discharged body fluids are well known in the art. Such absorbent products generally comprise a fibrous mass or other absorbent body which can absorb and hold the body fluids. Similarly, it is well known that feminine care articles have been employed to absorb and hold liquids, such as urine and/or menses. The absorbent articles have included various systems of liquid-handling layers, such as intake layers, distribution layers, retention layers and the like. Particular absorbent articles have included sections that could be separated away to change the size and shape of the remaining article. Additionally, the separated sections of the articles could be independently used as individual absorbent articles. Conventional absorbent articles have also included attachment systems, such as garment adhesives or mechanical fasteners, for securing the article to the crotch region of a wearer's undergarment. Particular arrangements have included wing portions which can help to hold the article in place at a selected location in the wearer's undergarment. Various fasteners have been employed to secure the wing portions in a desired configuration during ordinary use. The fasteners have included adhesive fasteners as well as mechanical fasteners, and the mechanical fasteners have included conventional, hook-and-loop fasteners.

Conventional absorbent articles, however, have not provided desired combinations of comfort, and versatility, and have not been sufficiently adaptable to match the varying needs of the individual user. In particular, the articles have not been sufficiently able to provide the different levels of absorbency, area coverage and protection that have been desired at different times during the periodic use-cycle of the individual wearer. The conventional articles have not been sufficiently versatile to accommodate use with different styles of undergarments. As a result, there has been a continued need for improved absorbent articles that are more readily adaptable to the needs of the individual user while providing secure levels of liquid intake and storage, along with desired levels of comfort.

BRIEF DESCRIPTION OF THE INVENTION

Generally stated, the present invention provides an absorbent article which can include a first pad section, and a relatively smaller second pad section which is operatively joined to the first pad section. The first pad section can include a first body-side cover, a first backsheet, a first absorbent body located between the first cover and the first backsheet, and a first garment-attachment mechanism located on a garment-side surface of the first backsheet. The second pad section can include a second body-side cover, a second backsheet, a second absorbent body located between the second cover and the second backsheet, and a second garment-attachment mechanism located on the garment-side surface of the second backsheet. In a particular aspect, the first pad section and the second pad section can at least partially overlap with each other. In another aspect, the first pad section can overlap at least a portion of a body-side surface of the second pad section. With still another aspect, at least a portion of the first backsheet can be configured to overlap at least an adjacent portion of a body-side surface of the second cover. In a further aspect, at least a portion of the first garment-attachment mechanism can operatively attach the first pad section to the second pad section.

By incorporating its various features and configurations, the article of the invention can be configured to be more readily adaptable to match the varying needs of the individual user. The articles can have an improved ability to provide the different levels of absorbency, area coverage and protection that have been desired at different times during the use cycle of the individual user. The articles can also be more versatile to better accommodate use with different styles of undergarments. As a result, the invention can provide an improved absorbent article that are more readily adaptable to the needs of the individual user while providing secure levels of liquid intake and storage, along with desired levels of comfort.

BRIEF DESCRIPTION OF THE DRAWINGS

The various features, aspects and advantages of the present invention will become better understood with reference to the following description, appended claims and accompanying drawings where:

DETAILED DESCRIPTION OF THE INVENTION

Figure 1:
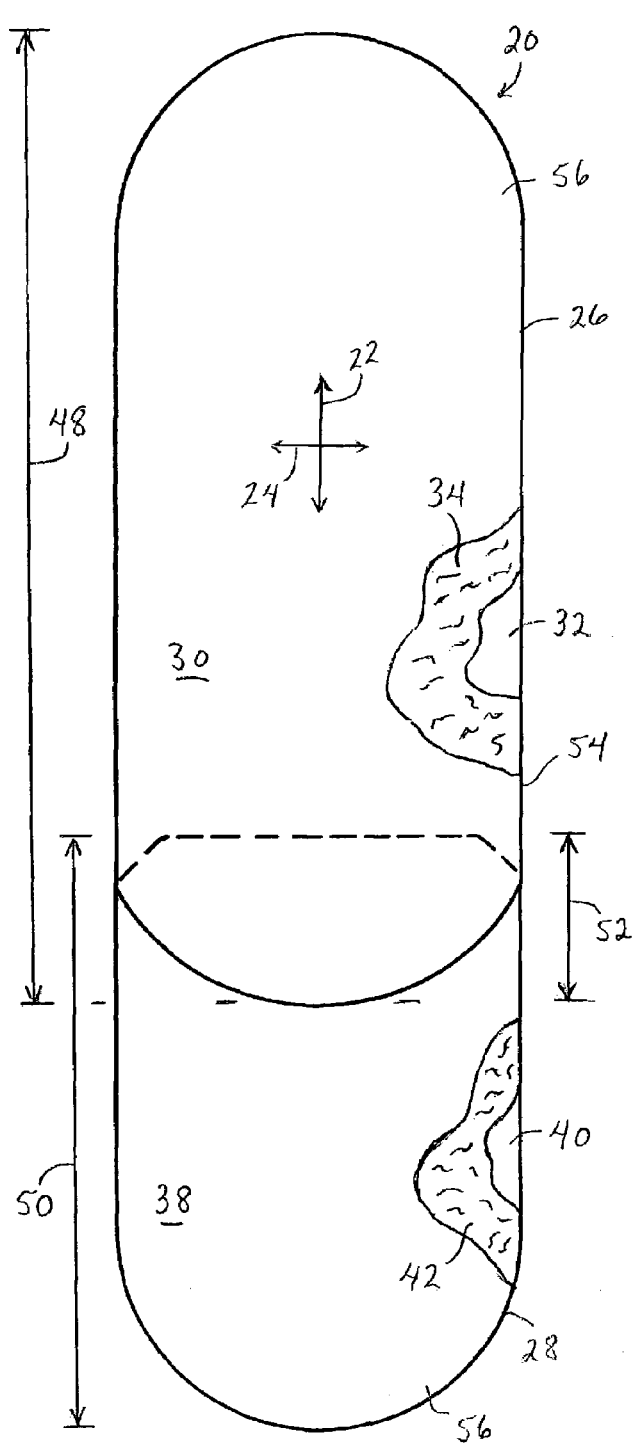
FIG. 1 shows a representative, partially cut-away, plan view of a bodyside of an absorbent article that incorporates the present invention.

It should be noted that, when employed in the present disclosure, the terms "comprises", "comprising" and other derivatives from the root term "comprise" are intended to be open-ended terms that specify the presence of any stated features, elements, integers, steps, or components, and are not intended to preclude the presence or addition of one or more other features, elements, integers, steps, components, or groups thereof.

By the terms "particle," "particles," "particulate," "particulates" and the like, it is meant that the material is generally in the form of individually separate, discrete units. The units can comprise granules, powders, spheres, pulverized materials or the like, as well as combinations thereof. The particles can have any desired shape such as, for example, cubic, rod-like, polyhedral, spherical or semi-spherical, rounded or semi-rounded, angular, irregular, etc. Shapes having a large greatest dimension/smallest dimension ratio, such as needles, flakes and fibers, are also contemplated for inclusion herein. The terms "particle" or "particulate" may also include an agglomeration comprising more than one individual particle, particulate or the like. Additionally, a particle, particulate or any desired agglomeration thereof may be composed of more than one type of material.

As used herein, the term "nonwoven" refers to a fabric web that has a structure of individual fibers or filaments which are interlaid, but not in an identifiable repeating manner.

As used herein, the terms "spunbond" or "spunbonded fiber" refer to fibers which are formed by extruding filaments of molten thermoplastic material from a plurality of fine, usually circular, capillaries of a spinneret, and then rapidly reducing the diameter of the extruded filaments.

As used herein, the phrase "meltblown fibers" refers to fibers formed by extruding a molten thermoplastic material through a plurality of fine, usually circular, die capillaries as molten threads or filaments into a high velocity, usually heated, gas (e.g., air) stream which attenuates the filaments of molten thermoplastic material to reduce their diameter. Thereafter, the meltblown fibers are carried by the high velocity gas stream and are deposited on a collecting surface to form a web of randomly disbursed meltblown fibers.

"Coform" as used herein is intended to describe a blend of meltblown fibers and cellulose fibers that is formed by air forming a meltblown polymer material while simultaneously blowing air-suspended cellulose fibers into the stream of meltblown fibers. The meltblown fibers containing wood fibers are collected on a forming surface, such as provided by a foraminous belt. The forming surface may include a gas-pervious material, such as spunbonded fabric material, that has been placed onto the forming surface.

As used herein, the phrase "complex liquid" describes a liquid generally characterized as being a viscoelastic liquid comprising multiple components having inhomogeneous physical and/or chemical properties. It is the inhomogeneous properties of the multiple components that challenge the efficacy of an absorbent or adsorbent material in the handling of complex liquids. In contrast with complex liquids, simple liquids, such as, for example, urine, physiological saline, water and the like, are generally characterized as being relatively low-viscosity and comprising one or more components having homogeneous physical and/or chemical properties. As a result of having homogeneous properties, the one or more components of simple liquids behave substantially similarly during absorption or adsorption, although some components may be absorbed or adsorbed more readily than others.

Although a complex liquid is generally characterized herein as including specific components having inhomogeneous properties, each specific component of a complex liquid generally has homogeneous properties. Consider for example a representative complex body-liquid having three specific components: red blood cells, blood protein molecules and water molecules. Upon examination, one skilled in the art could easily distinguish between each of the three specific components according to their generally inhomogeneous properties. Moreover, when examining a particular specific component such as the red blood cell component, one skilled in the art could easily recognize the generally homogeneous properties of the red blood cells.

As used herein, the term "hydrophilic" describes fibers or the surfaces of fibers that are wetted by the aqueous liquids in contact with the fibers. The degree of wetting of the materials can, in turn, be described in terms of the contact angles and the surface tensions of the liquids and materials involved. Equipment and techniques suitable for measuring the wettability of particular fiber materials can be provided by a Cahn SFA-222 Surface Force Analyzer System, or a substantially equivalent system. When measured with this system, fibers having contact angles less than 90° are designated "wettable" or hydrophilic, while fibers having contact angles equal to or greater than to 90° are designated "nonwettable" or hydrophobic. When comparing materials, a material that forms a relatively larger contact angle with water is relatively less hydrophilic than a material that forms a smaller contact angle with water.

As used herein, the phrase "absorbent article" refers to devices which absorb and contain body liquids, and more specifically, refers to devices which are placed against or near the skin to absorb and contain the various liquids discharged from the body. The term "disposable" is used herein to describe absorbent articles that are not intended to be laundered or otherwise restored or reused as an absorbent article after a single use. Examples of such disposable absorbent articles include, but are not limited to: health care related products including surgical drapes, gowns, and sterile wraps; personal care absorbent products such as feminine hygiene products (e.g., sanitary napkins, pantiliners, tampons, interlabial devices and the like), infant diapers, children's training pants, adult incontinence products and the like; as well as absorbent wipes and covering mats.

Disposable absorbent articles such as, for example, many of the feminine care absorbent products, can include a liquid-pervious cover or topsheet, a substantially liquid-impervious backsheet joined to the topsheet, and an absorbent core structure positioned and held between the topsheet and the backsheet. The topsheet is operatively permeable to the liquids that are intended to be held or stored by the absorbent article, and the backsheet may be substantially impermeable or otherwise operatively impermeable to the intended liquids. The absorbent article may also include other components, such as liquid wicking layers, liquid intake layers, liquid distribution layers, transfer layers, barrier layers, and the like, as well as combinations thereof. Disposable absorbent articles and the components thereof can operate to provide a body-facing surface and a garment-facing surface. As used herein, the body-facing or bodyside surface means that surface of the article or component which is intended to be disposed toward or placed adjacent to the body of the wearer during ordinary use, while the outward, outward-facing or garment-side surface is on the opposite side, and is intended to be disposed to face away from the wearer's body during ordinary use. Such outward surface may be arranged to face toward or placed adjacent to the wearer's undergarments when the absorbent article is worn.

Figure 2:
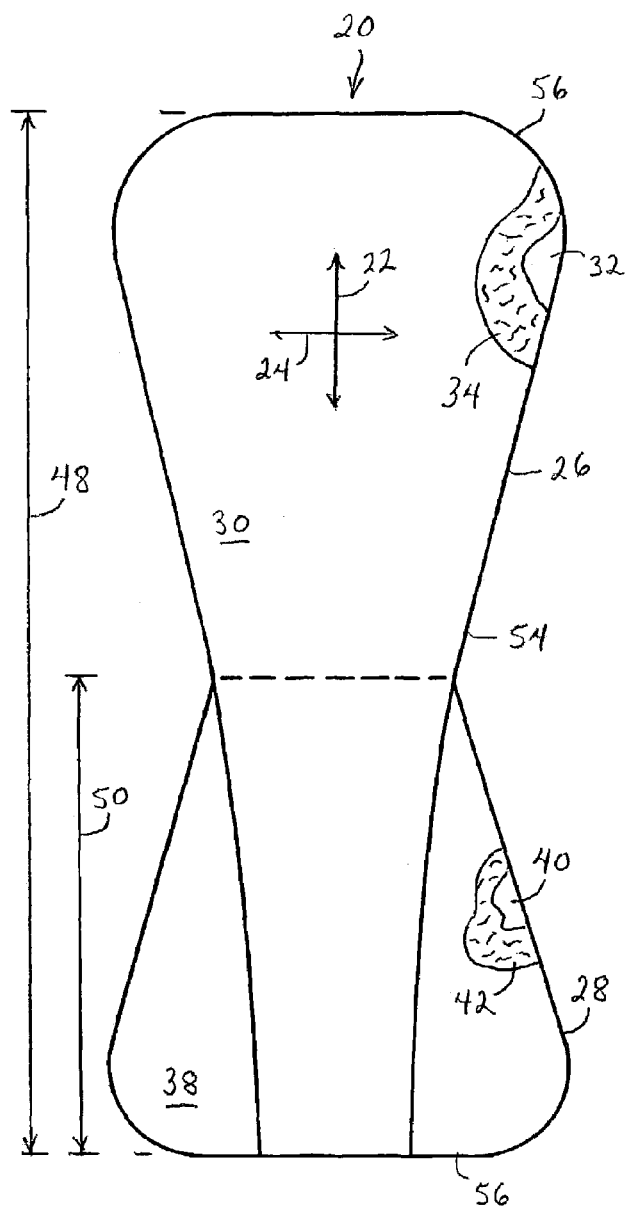
FIG. 2 shows a representative, partially cut-away, plan view of a bodyside of another absorbent article that incorporates the present invention.

FIGS. 1 and 2 illustrate examples of a suitable article, such as the representatively shown feminine care article, which is configured to incorporate the present invention. As representatively shown, the overall complete absorbent article 20 can provide a modular, primary absorbent feminine care article. In desired configurations, the absorbent article can be a pantyliner or other absorbent pad that is intended for use with a wearer's undergarment. The article 20 can have a lengthwise longitudinal direction 22, a transverse, laterally extending, cross-direction 24, first and second longitudinally opposed end portions 56, and an intermediate portion 54 located between the end portions. As representatively shown, the longitudinal dimension of the article is relatively larger than the lateral dimension of the article. The overall, primary article 20 can include an overall topsheet or cover (e.g. such as provided by a combination of topsheet members 30 and 38); an overall backsheet (e.g. such as provide by a combination of backsheet members 32 and 40); and an overall absorbent structure (e.g. such as provided by a combination of absorbent body members 34 and 42).

The article 20 can include a first pad section 26, and a relatively smaller second pad section 28 which is operatively joined to the first pad section. The first pad section 26 can include a first body-side cover 30, a first backsheet 32, and a first absorbent body 34 which is operatively located and sandwiched between the first cover 30 and the first backsheet 32. Additionally, a first region of a first garment-attachment mechanism 36 can be located on a garment-side surface of the first backsheet 32. The second pad section 28 can include a second body-side cover 38, a second backsheet 40, and a second absorbent body 42 which is operatively located and sandwiched between the second cover 38 and the second backsheet 40. Additionally, a second region of a second garment-attachment mechanism 44 can be located on the garment-side surface of the second backsheet 40. In a particular aspect, the first pad section 26 and the second pad section 28 can at least partially overlap with each other. In another aspect, the first pad section 26 can overlap onto at least a portion of either a garment-side or body-side surface of the second pad section 28. In still another aspect, at least a portion of the first backsheet 32 can be configured to overlap at least an adjacent portion of a body-side' surface of the second cover 38. In a further aspect, at least a portion of the first region of the first garment-attachment mechanism 36 can operatively attach or otherwise interconnect the first pad section 26 to the second pad section 28. Optionally, at least a portion of the second region of the second garment-attachment mechanism 44 can operatively attach or otherwise interconnect the second pad section 28 to the first pad section 26. In a desired configuration, for example, the first garment-attachment mechanism 36 can operatively attach or otherwise interconnect at least a portion of the first backsheet 32 to at least a portion of the second cover 38.

By incorporating its various features, aspects and configurations, alone or in desired combinations, the article of the invention can include a distinctive, modular configuration that allows increased versatility. The article can be selectively modified to better match the size and/or shape of the article to the particular needs of the individual user. As a result, an individual user can selectively rearrange or otherwise modify the article to provide desired configurations of size, shape and absorbent capacity. Desired arrangements can provide improved appearance and aesthetics. As a result, the article of the invention can provide greater versatility and adaptability while providing desired levels of absorbent capacity, comfort and fit. The representatively shown configurations, for example, can provide a distinctive "3-in-1" modular article, where three different use configurations can be derived from a single primary article.

The topsheet members 30 and 38 may include a layer constructed of any operative material, and may include a composite material. For example, the topsheet member can include a woven fabric, a nonwoven fabric, a polymer film, a film-fabric laminate or the like, as well as combinations thereof. Examples of a nonwoven fabric include spunbond fabric, meltblown fabric, conform fabric, a carded web, a bonded-carded-web, a bicomponent spunbond fabric or the like as well as combinations thereof. For example, the topsheet member can include a woven fabric, a nonwoven fabric, a polymeric film that has been configured to be operatively liquid-permeable, or the like, as well as combinations thereof. Other examples of suitable materials for constructing the topsheet member can include rayon, bonded carded webs of polyester, polypropylene, polyethylene, nylon, or other heat-bondable fibers, polyolefins, such as copolymers of polypropylene and polyethylene, linear low-density polyethylene, aliphatic esters such as polylactic acid, finely perforated film webs, net materials, and the like, as well as combinations thereof.

A more particular example of a suitable material for the topsheet layer or member can include a bonded-carded-web composed of polypropylene and polyethylene, such as has been used as a cover stock for KOTEX brand pantiliners, and has been obtainable from Vliesstoffwerk Christian Heinrich Sandler GmbH & Co. KG, a business having an address at Postfach 1144, D95120 Schwarzenbach/Saale, Germany. Other examples of suitable topsheet materials are composite materials of a polymer and a nonwoven fabric material. The composite materials are typically in the form of integral sheets generally formed by the extrusion of a polymer onto a web of spunbond material. In a desired arrangement, the topsheet member can be configured to be operatively liquid-permeable with regard to the liquids that the article is intended to absorb or otherwise handle. The operative liquid-permeability may, for example be provided by a plurality of pores, perforations, apertures or other openings, as well as combinations thereof, that are present or formed in the topsheet member. The apertures or other openings can help increase the rate at which bodily liquids can move through the thickness of the topsheet member and penetrate into the other components of the article (e.g. into the absorbent structure). The selected arrangement of liquid-permeability is desirably present at least on an operative portion of the topsheet member that is appointed for placement on the bodyside of the article. The topsheet member can provide comfort and conformability, and can function to direct bodily exudates away from the body and toward the absorbent structure. In a desired feature, the topsheet member can be configured to retain little or no liquid in its structure, and can be configured to provide a relatively comfortable and non-irritating surface next to the body-tissues of a female wearer. The topsheet member can be constructed of any material which is also easily penetrated by bodily fluids that contact the surface of the topsheet member.

The topsheet layer or member can also have at least a portion of its bodyside surface treated with a surfactant to render the topsheet member more hydrophilic. The surfactant can permit arriving bodily liquids to more readily penetrate the topsheet member. The surfactant may also diminish the likelihood that the arriving bodily fluids, such as menstrual fluid, will flow off the topsheet member rather than penetrate through the topsheet member into other components of the article (e.g. into the structure of the absorbent body members). In a particular configuration, the surfactant can be substantially evenly distributed across at least a portion of the upper, bodyside surface of the topsheet member that overlays the upper, bodyside surface of its corresponding absorbent body member.

The topsheet member may be maintained in secured relation with its corresponding absorbent body member by bonding all or a portion of the adjacent surfaces to one another. A variety of bonding mechanisms or systems known to one of skill in the art may be utilized to achieve any such secured relation. Examples of such mechanisms include, but are not limited to, the application of adhesives in a variety of patterns between the two adjoining surfaces, entangling at least portions of the adjacent surface of the absorbent with portions of the adjacent surface of the topsheet member, or fusing at least portions of the adjacent surface of the topsheet member to portions of the adjacent surface of the absorbent.

The topsheet member typically extends over the upper, bodyside surface of its corresponding absorbent body member, but can alternatively extend around its corresponding pad section to partially or entirely, surround or enclose its corresponding absorbent body member. In other arrangements, the topsheet member and its corresponding backsheet member may or may not have peripheral margins which extend outwardly beyond the terminal, peripheral edges of their corresponding absorbent body member. Where the article includes the peripheral margins, the extending margins can be partially or entirely joined together to surround or enclose their corresponding absorbent body member.

The backsheet members 32 and 40 may include a layer constructed of any operative material, and may or may not have a selected level of liquid-permeability or liquid-impermeability, as desired. In a particular configuration, the individual backsheet member may be configured to provide an operatively liquid-impermeable structure of the backsheet member. The backsheet member may, for example, include a polymeric film, a woven fabric, a nonwoven fabric or the like, as well as combinations or composites thereof. For example, the backsheet member may include a polymer film laminated to a woven or nonwoven fabric. In a particular feature, the polymer film can be composed of polyethylene, polypropylene, polyester or the like, as well as combinations thereof. Additionally, the polymer film may be micro-embossed, have a printed design, have a printed message to the consumer, and/or may be at least partially colored. Desirably, the backsheet member can operatively permit a sufficient passage of air and moisture vapor out of the article, particularly out of an absorbent structure, while blocking the passage of bodily liquids. An example of a suitable material for the backsheet member can include a breathable, microporous film, such as a HANJIN Breathable Baffle available from Hanjin Printing, Hanjin P&C Company Limited, a business having offices located in Sahvon-li.Jungan-mvu.Kongiu-City, Chungcheong nam-do, Republic of South Korea. The backsheet material is a breathable film, which is white in color, dimple embossed and contains: 47.78% calcium carbonate, 2.22% TiO2, and 50% polyethylene.

In a particular feature, the polymer film can have a minimum thickness of no less than about 0.025 mm, and in another feature, the polymer film can have a maximum thickness of no greater than about 0.13 mm. Bicomponent films or other multi-component films can also be used, as well as woven and/or nonwoven fabrics which have been treated to render them operatively liquid-impermeable. Another suitable backsheet member material can include a closed cell polyolefin foam. For example, a closed cell polyethylene foam may be employed. Still another example of a backsheet member material would be a material that is similar to a polyethylene film which is used on commercially sold KOTEX brand pantiliners, and is obtainable from Pliant Corporation, a business having offices located in Schaumburg, Ill., USA.

The structure of the absorbent body members 34 and 42 can be operatively configured to provide a desired level of absorbent retention or storage capacity. More particularly, the individual absorbent body member can be configured to hold a liquid, such as urine, menses, other complex liquid or the like, as well as combinations thereof. As representatively shown, the absorbent body member can include a matrix of absorbent fibers and/or absorbent particulate material. The absorbent body member may, for example, include natural fibers, synthetic fibers, superabsorbent materials, a woven fabric; a nonwoven fabric; a conform web; a wet-laid fibrous web; a substantially unbonded airlaid fibrous web; an operatively bonded, stabilized-airlaid fibrous web; or the like, as well as combinations thereof. Additionally, the absorbent body may include one or more components that can modify menses or inter-menstrual liquid.

Superabsorbent materials suitable for use in the present invention are known to those skilled in the art, and may be in any operative form, such as particulate form. Generally stated, the superabsorbent material can be a water-swellable, generally water-insoluble, hydrogel-forming polymeric absorbent material, which is capable of absorbing at least about 20, desirably about 30, and possibly about 60 times or more its weight in physiological saline (e.g. saline with 0.9 wt % NaCl). The hydrogel-forming polymeric absorbent material may be formed from organic hydrogel-forming polymeric material, which may include natural material such as agar, pectin, and guar gum; modified natural materials such as carboxymethyl cellulose, carboxyethyl cellulose, and hydroxypropyl cellulose; and synthetic hydrogel-forming polymers. Synthetic hydrogel-forming polymers include, for example, alkali metal salts of polyacrylic acid, polyacrylamides, polyvinyl alcohol, ethylene maleic anhydride copolymers, polyvinyl ethers, polyvinyl morpholinone, polymers and copolymers of vinyl sulfonic acid, polyacrylates, polyacrylamides, polyvinyl pyridine, and the like. Other suitable hydrogel-forming polymers include hydrolyzed acrylonitrile grafted starch, acrylic acid grafted starch, and isobutylene maleic anhydride copolymers and mixtures thereof. The hydrogel-forming polymers are preferably lightly crosslinked to render the material substantially water insoluble. Crosslinking may, for example, be by irradiation or covalent, ionic, Van der Waals, or hydrogen bonding. Suitable materials are available from various commercial vendors such as The Dow Chemical Company and Stockhausen, Inc. The superabsorbent material may desirably be included in an appointed storage or retention portion of the absorbent system, and may optionally be employed in other components or portions of the absorbent article.

The amount of superabsorbent material in an individual absorbent body member 34 and/or 42 can be at least a minimum of about 5 wt %, as determined with respect to the total weight of material in the corresponding absorbent body member 34 or 42. The amount of superabsorbent material can alternatively be at least about 8 wt %, and can optionally be at least about 10 wt % to provide improved performance. In other aspects, the amount of superabsorbent material can be up to a maximum of about 75 wt %, or more. The amount of superabsorbent material can alternatively be up to about 38 wt %, and can optionally be up to about 20 wt % to provide improved effectiveness. In desired configurations, the amount of superabsorbent can be about 15 wt %.

In particular configurations, the absorbent article 20 and its associated absorbent body members (e.g. absorbent members 34 and 42) can be configured to provide a composite, modular absorbent structure. Additionally, the absorbent body members can together provide a composite, overall absorbent saturation capacity which totals at least a minimum of about 5 grams of menses simulant A. The total, overall absorbent saturation capacity can alternatively be at least about 40 grams of menses simulant A to provide improved performance. In other aspects, the total overall absorbent saturation capacity of the absorbent members can be up to a maximum of about 120 grams of menses simulant A, or more, and can alternatively be up to about 88 grams of menses simulant A to provide improved effectiveness. In a desired arrangement, the total composite absorbent saturation capacity can be about 60 grams of menses simulant A.

In a desired feature, the relatively larger absorbent body member 34 can provide at least a minimum of about 55% of the total absorbent capacity. The relatively larger absorbent body member can alternatively provide at least about 60% of the total absorbent capacity, and can optionally provide at least about 70% of the total absorbent capacity. In another feature, the relatively larger absorbent body member 34 can provide up to a maximum of about 90% of the total absorbent capacity. The relatively larger absorbent body member can alternatively provide up to about 80% of the total absorbent capacity to provide an improved performance of the module that includes the first pad section 26. The remaining percentage of the total absorbent capacity can be provided by the relatively smaller absorbent body member 42, with the ordinary understanding that the percentages of the absorbent capacities provided by the various absorbent members will total 100%.

The menses simulant A is composed of swine blood diluted with swine plasma to provide a hematocrit level of 35% (by volume). A suitable device for determining the hematocrit level is a HEMATOSTAT-2 system, available from Separation Technology, Inc., a business having offices located in Altamonte Springs, Fla., U.S.A. A substantially equivalent system may alternatively be employed. Simulant A is typically used for absorbent capacity tests, where the viscoelastic properties that affect liquid movement have been found to be of little importance.

A specific saturation capacity and a specific retention capacity of an absorbent body member or other absorbent component can be determined by soaking a 1 inch by 1 inch (2.54 cm×2.54 cm) sample of absorbent material in an amount of simulant A that is sufficient to fully saturate the sample (e.g. 30 mL) for 30 minutes. The wet absorbent is then placed between a layer of through-air-bonded-carded web material and a layer of blotter paper, and a pressure of 0.05 psi (0.345 KPa) is applied for 1 minute to remove any pools of liquid. The saturated sample is then weighed. The weight of liquid held in the sample divided by the dry weight of the sample is the specific saturation capacity of the sample.

After the saturated sampled is weighed, the absorbent sample is placed in a centrifuge and spun at 300 G for 3 minutes. The spun sample is then weighed. The weight of the liquid remaining in the spun sample divided by the dry weight of the sample is the specific retention capacity of the sample.

Accordingly:

a. Saturation Capacity=(Wet Wt. Before Centrifuge−Dry Wt.)/(Dry Wt.)

b. Retention Capacity=(Wet Wt. After Centrifuge−Dry Wt.)/(Dry Wt.)

The total absorbent saturation capacity of an overall layer or other component can be determined by multiplying its specific saturation capacity times the total weight of such component. Similarly, total absorbent retention capacity of an overall layer or other component can be determined by multiplying its specific retention capacity times the total weight of such component.

For the absorbent capacity determinations, a suitable through-air-bonded-carded web material has a 2.5 osy (84.8 g/m$^2$) basis weight, a 0.024 g/cm$^3$ density, and is composed of 60 wt % of 6 denier, KoSa type 295 polyester fiber; and 40 wt % of 3 denier, Chisso ESC-HR6 bicomponent fiber. The polyester fiber is available from KoSa, a business having offices located in Charlotte, N.C., U.S.A., and the bicomponent fiber is available from Chisso Corporation, a business having offices located in Osaka, Japan. A suitable blotter paper is 100-lb VERIGOOD white blotter paper available from Fort James Corporation, a business having offices located in Menasha, Wis., U.S.A. (e.g. product item number 411-01012). Substantially equivalent materials may optionally be employed.

Figure 1A:
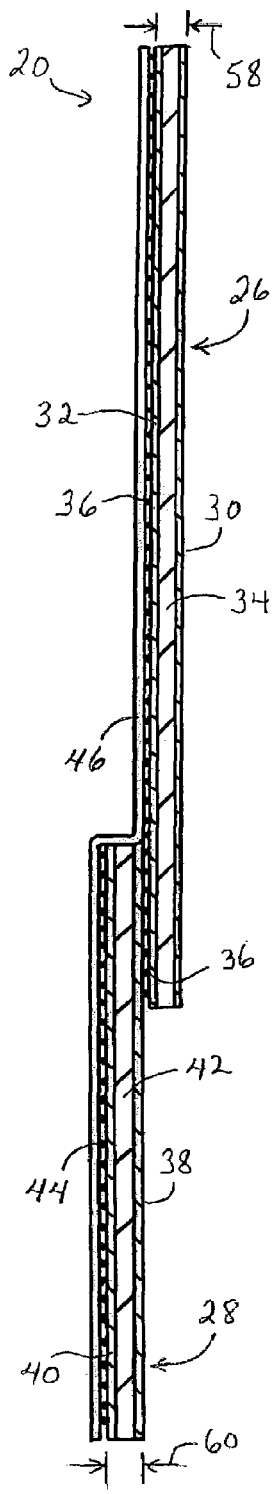
FIG. 1A shows a representative view of a longitudinal cross-section through the absorbent article illustrated in FIG. 1.
Figure 2A:
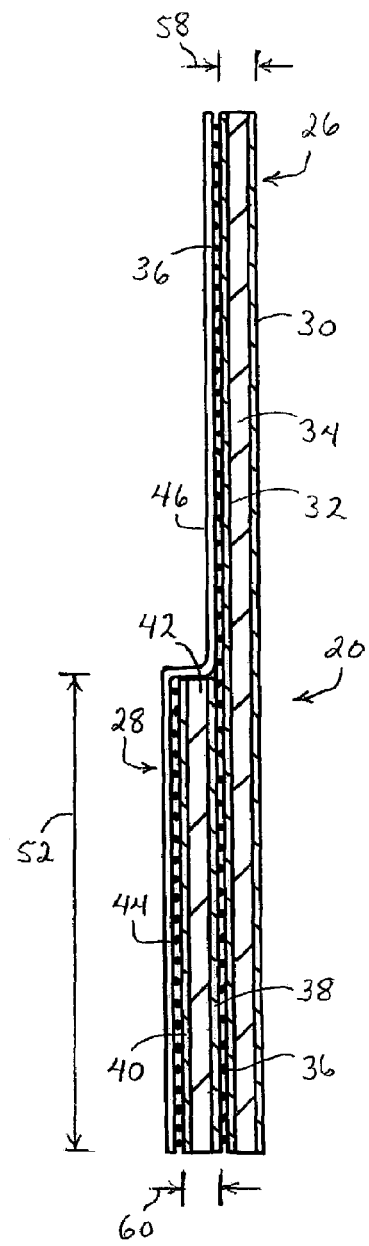
FIG. 2A shows a representative view of a longitudinal cross-section through the absorbent article illustrated in FIG. 2.

As representatively shown, the absorbent structure of the overall, primary article 20 can comprise a composite structure having a selected plurality of strata or layers. With reference to FIGS. 1A and 2A, for example, the composite absorbent structure can include the first absorbent body member 34 and the second absorbent body member 42, as well as any other desired components, arranged in any operative combination. As representatively shown, the absorbent structure can include the first absorbent body member 34 which is positioned between the first topsheet member 30 and the first backsheet member 32, and the second absorbent body member 42 which is positioned between the second topsheet member 38 and the second backsheet member 40.

In a particular arrangement, the absorbent body members 34 and/or 42 can include a thermally-bonded, stabilized airlaid fibrous web (e.g. Concert code 175.1020) available from Concert Fabrication, a business having offices located in Gatineaux, Quebec, Canada. The absorbent body member may optionally include a similar, stabilized airlaid fibrous web available from Buckeye Technologies, Inc., a business having offices located in Memphis, Tenn., U.S.A.

The first absorbent body member 34 can have a basis weight which differs from or substantially equals the basis weight of the second absorbent body member 42. In particular arrangements, the basis weight of the absorbent body members 34 and 42 can be at least a minimum of about 50 g/m$^2$. The basis weight of the intake layer can alternatively be at least about 80 g/m$^2$, and can optionally be at least about 100 g/m$^2$ to provide improved performance. Additionally, the basis weight of the intake layer can be up to a maximum of about 400 g/m$^2$, or more. The basis weight of the intake layer can alternatively be up to about 280 g/m$^2$, and can optionally be up to about 140 g/m$^2$ to provide improved effectiveness. Such arrangements can, for example, be suitable for absorbent members employed in absorbent pantiliners articles.

In other arrangements, the basis weight of the absorbent body members 34 and 42 can be at least a minimum of about 100 g/m$^2$. The basis weight of the intake layer can alternatively be at least about 200 g/m$^2$, and can optionally be at least about 250 g/m$^2$ to provide improved performance. Additionally, the basis weight of the intake layer can be up to a maximum of about 600 g/m$^2$, or more. The basis weight of the intake layer can alternatively be up to about 350 g/m$^2$, and can optionally be up to about 300 g/m$^2$ to provide improved effectiveness. Such arrangements can, for example, be suitable for absorbent members employed in absorbent "ultrathin" pad articles.

If the basis weight of the absorbent members is outside the desired values, the article can be too thick and bulky, and can provide poor comfort and excessive awareness of the article during use. Additionally, the absorbent members can be excessively expensive.

The absorbent body members 34 and/or 42 may have any operative shape and/or design. For example, the absorbent body members may include a single piece of material, or multiple pieces of material, such as multiple strips of material. In addition, the first absorbent body member 34 may include holes or apertures to help provide desired liquid-intake properties. The apertures may extend partially or completely through the z-directional thickness of the absorbent body members 34 and/or 42, as desired.

Figure 1B:
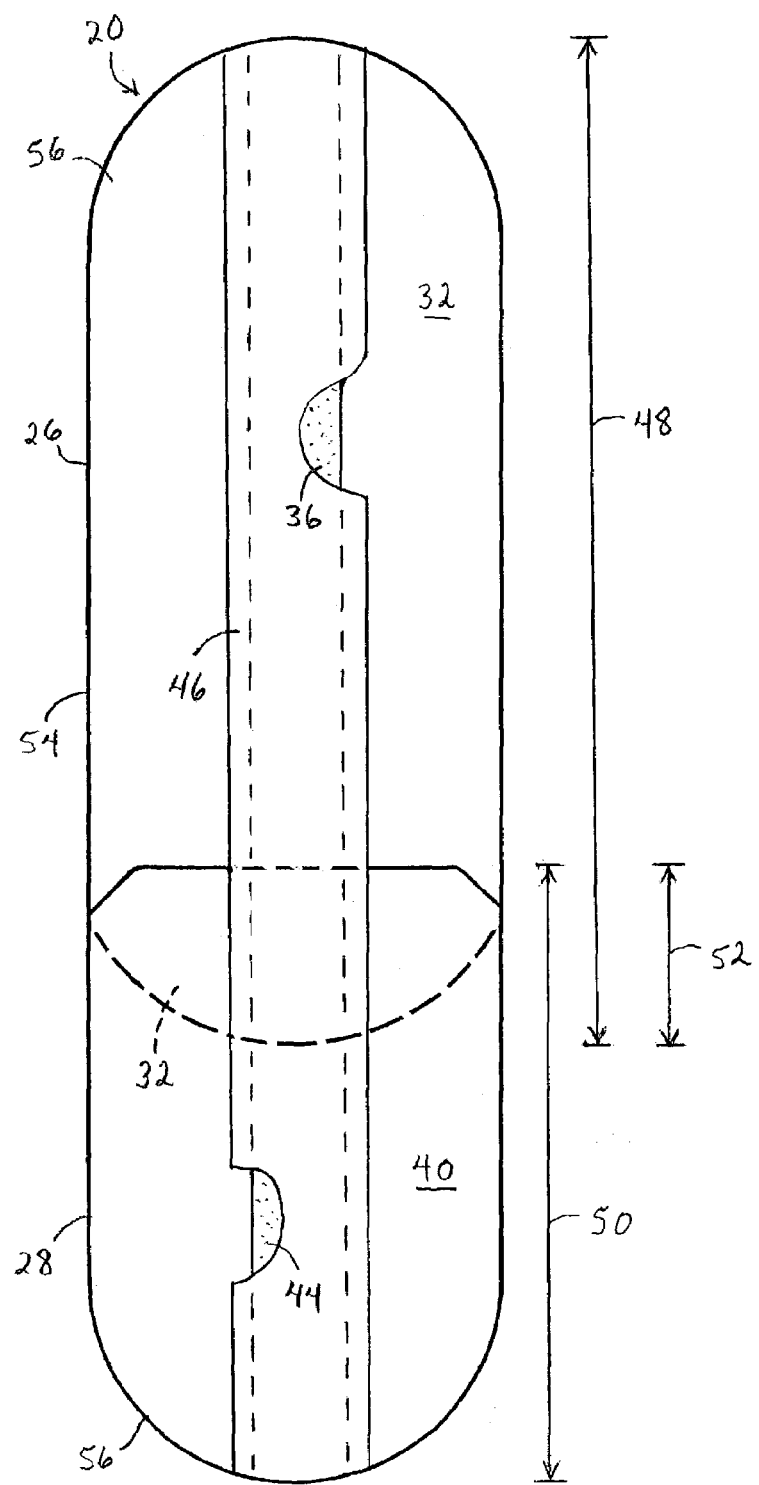
FIG. 1B shows a representative, partially cut-away, plan view of a garment-side of the absorbent article illustrated in FIG. 1.

With reference to FIGS. 1 through 1B, the first pad section 26 can be configured to only partially overlap with the second pad section 28. Additionally, the second pad section 28 can be configured to only partially overlap with either the bodyside or garment-side of the first pad section 26. More particularly, the first absorbent body member 34 can be configured to only partially overlap with the body-side or garment-side of the second absorbent body member 42. Accordingly, at least a significant portion of the first absorbent body 34 can extend longitudinally beyond a terminal end edge of the second absorbent body 42. Additionally, at least a significant portion of the second absorbent body 42 can extend longitudinally beyond a terminal end edge of the first absorbent body 34.

Figure 2B:
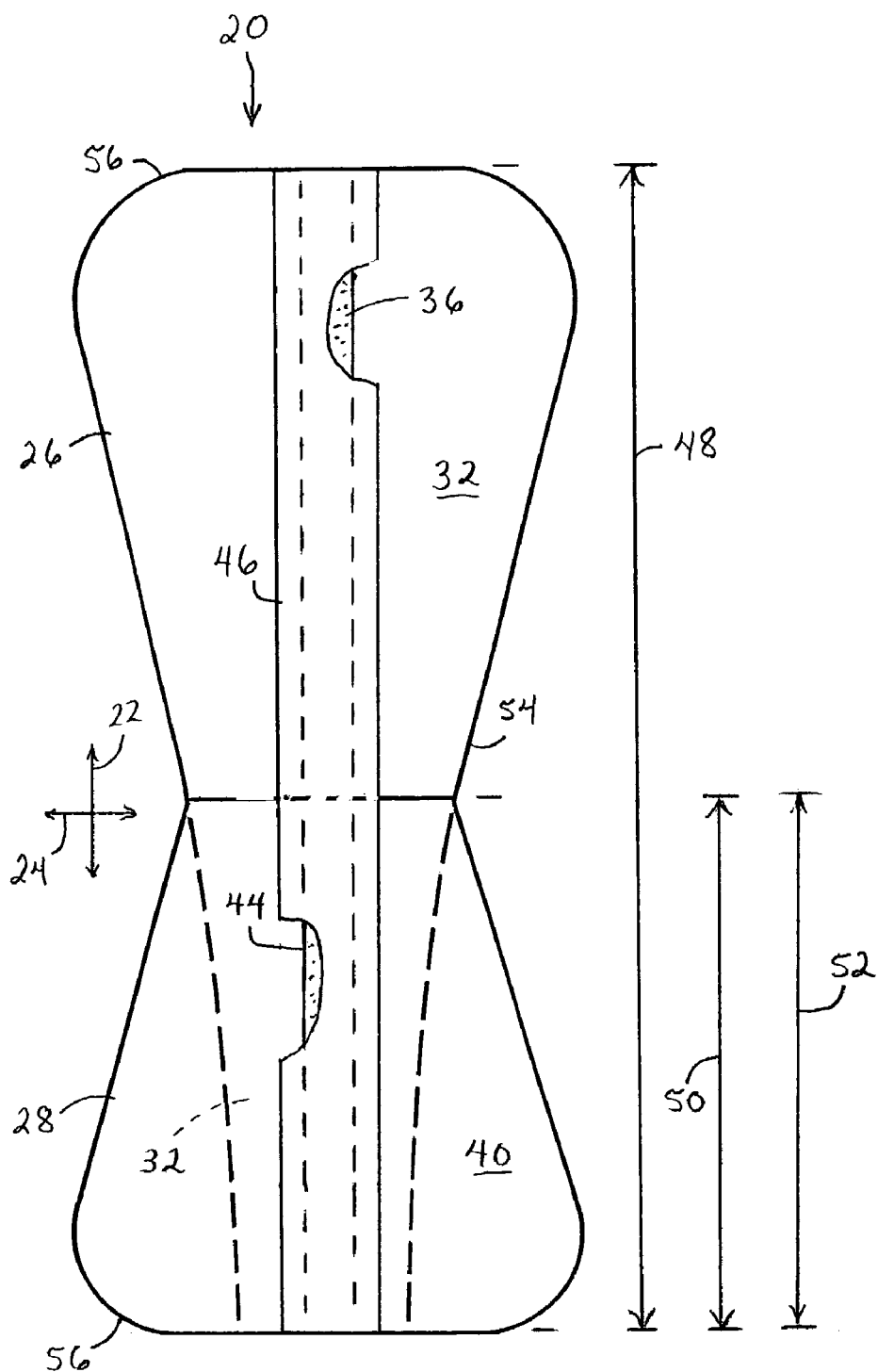
FIG. 2B shows a representative, partially cut-away, plan view of a garment-side of the absorbent article illustrated in FIG. 2.

With reference to FIGS. 2 through 2B, the first pad section 26 can be configured to overlap the entirety of the second pad section 28, and the second pad section 28 can be configured to overlap only a limited part of the first pad section 26. Accordingly, at least one end portion of the first pad section 26 can extend longitudinally beyond a terminal end edge of the second pad section 28. A longitudinally opposed, second end portion of the first pad section 26 can be coterminous with a second, terminal end edge of the second pad section 28, or may optionally extend longitudinally beyond the second, terminal end edge of the second pad section 28.

In the various arrangements of the article 20, the first and second garment-attachment mechanisms 36 and/or 44 can be provided by any operative, conventional attachment system. Examples of such systems can include, for example, adhesives, cohesives, inter-engaging mechanical fastener systems or the like, as well as combinations thereof. For example, the attachment mechanism may include an extending "hook" component in a hook-and-loop attachment system. In the example of the representatively shown configuration, the first garment-attachment mechanism 36 can include a first-garment adhesive, and the second garment-attachment mechanism 44 can include a second garment-adhesive. Such garment adhesives are commercially available, and are well known in the art.

With reference to FIGS. 1A, 1B, 2A and 2B, the first garment-attachment mechanism 36 can be operatively joined to the first pad section 26. As representatively shown, the first garment-attachment mechanism can be operatively joined to the garment-side of the first backsheet member 32. The first garment-attachment mechanism may extend the entire longitudinal length of the first pad section, but may optionally extend along only a limited portion of the longitudinal length of the first pad section 26, as desired. Similarly, the second garment-attachment mechanism 44 can be operatively joined to the second pad section 28. The second garment-attachment mechanism may extend the entire longitudinal length of the second pad section, or may optionally extend along only a limited portion of the longitudinal length of the second pad section 28, as desired.

The first pad section 26 can be releasably secured to the second pad section 28. As representatively shown, at least a portion of the first region of the first garment-attachment mechanism 36 can be configured to releasably attach or join the first pad section 26 to the second pad section 28. In a desired configuration, the first garment-attachment mechanism 36 can releasably attach or join at least a portion of the first backsheet 32 to at least a portion of the second cover 38. As a result, the first pad section 26 can be selectively separated away from the second pad section 28, and the first pad section can then be independently employed as a first module which provides a relatively reduced-size feminine care article. Additionally, the second pad section 28 can independently be employed as a second module which provides another, relatively reduced-size feminine care article.

Optionally, at least a portion of the second region of the second garment-attachment mechanism 44 can be configured to operatively attach or otherwise interconnect the second pad section 28 to the first pad section 26. In a particular arrangement, the second garment-attachment mechanism 44 can releasably attach or join at least a portion of the second backsheet 40 to at least a portion of the first cover 30.

A layer of protective strip material 46 can be disposed to operatively cover the exposed portions of the first garment-attachment mechanism 36 prior to use. Similarly, a layer of protective strip material can be disposed to operatively cover the exposed portions of the first garment-attachment mechanism 44. As representatively shown, a unitary strip of protective material can be employed to cover both the first and second garment-attachment mechanisms. In a particular feature, a frangible region of weakness can be located between a first portion of the protective strip material that covers the first garment-attachment mechanism 36 and a second portion of the protective strip material that covers the second garment-attachment mechanism 44. Optionally, a separate strip of protective material can be employed to cover the first garment-attachment mechanism 36, and another separate strip of protective material can be employed to cover the second garment-attachment mechanism 44. Where the first and second garment-attachment mechanisms are provided by adhesive, the protective strip can be provided by a layer of conventional release material. Such release materials are well known in the art and are available from commercial vendors.

In the various configurations of the article, the total overall absorbent article 20 can provide a primary absorbent article when the first pad section 26 is operatively assembled and attached to the second pad section 28. With reference to FIGS. 1 through 1B, the primary absorbent article 20 can, for example, provide a "long" or "extra-long" absorbent article. Additionally, the first pad section 26 can be independently employed to provide a relatively smaller "regular" absorbent article, and the second pad section 28 can be independently employed to provide another, relatively smaller "micro" absorbent article.

With reference to FIGS. 2 through 2B, the primary absorbent article 20 can alternatively provide a "regular" absorbent article. Additionally, the first pad section 26 can be independently employed to provide a "thong" absorbent article, and the second pad section 28 can be independently employed to provide a smaller, "micro" absorbent article.

As representatively shown in FIGS. 2 through 2B, the first pad section 26 can have a tapered shape which is configured to provide an operative absorbent liner for a "thong" undergarment when the first pad section 26 is independently worn. The tapered shape can have a gradually decreasing (or gradually increasing) cross-directional width dimension as one observes the pad width at different sequential locations along the longitudinal direction 22. A large section of the tapered shape can have a relatively largest cross-directional width of the first pad section, and can typically be appointed for placement toward the front side of the wearer's body. A small section of the tapered shape can include a relatively smallest cross-directional width of the first pad section, and can typically be appointed for placement toward the back or rear side of the wearer's body.

The second pad section 28 has a shape that cooperates with the tapered shape of the first pad section 26. Any operative shape may be employed in the second pad section 28. For example, a non-tapered shape may be employed for the second pad section 28. As illustrated in the representatively shown arrangement, the second pad section can have a second tapered shape, and the second tapered shape can differ from the shape of the first pad section 26. The second tapered shape can have a wide section and a narrow section. The wide section can include a widest cross-directional width of the second pad section 28, and the narrow section can have a narrowest cross-directional width of the second pad section.

When the second pad section 28 is independently worn, either the narrow or wider section of the second pad section can be appointed for placement toward the front side of the wearer's body, as desired. When the first and second pad sections 26 and 28 are operatively combined and assembled together, the overall perimeter of the primary article 20 can provide a generally hourglass shape, as representatively shown the in the example of the illustrated configuration.

In the various configurations of the invention, the first pad section 26 can have a selected area size. In particular arrangements, the area size of the first pad section 26 can be at least a minimum of about 60 cm$^2$. The area size can alternatively be at least about 68 cm$^2$, and can optionally be at least about 82 cm$^2$ to provide improved performance. In other aspects, the area size of the first pad section 26 can be up to a maximum of about 120 cm$^2$, or more. The area size can alternatively be up to about 110 cm$^2$, and can optionally be up to about 96 cm$^2$ to provide improved effectiveness. Such arrangements can, for example, be employed in the configurations of the first pad section 26 that are representatively shown in FIGS. 1 through 1B.

In other arrangements, the area size of the first pad section 26 can be at least a minimum of about 30 cm$^2$. The area size can alternatively be at least about 52 cm$^2$, and can optionally be at least about 61 cm$^2$ to provide improved performance. In other aspects, the area size of the first pad section 26 can be up to a maximum of about 80 cm$^2$, or more. The area size can alternatively be up to about 76 cm$^2$, and can optionally be up to about 72 cm$^2$ to provide improved effectiveness. Such arrangements can, for example, be employed in the configurations of the first pad section 26 that are representatively shown in FIGS. 2 through 2B.

Additionally, the second pad section 28 can have a selected area size. In a particular aspect, the area size of the second pad section 28 can be at least a minimum of about 3 cm$^2$. The area size can alternatively be at least about 4 cm$^2$, and can optionally be at least about 5 cm$^2$ to provide improved performance. In other aspects, the area size of the second pad section 28 can be up to a maximum of about 12 cm$^2$, or more. The area size can alternatively be up to about 11 cm$^2$, and can optionally be up to about 6 cm$^2$ to provide improved effectiveness.

If the area sizes of the pad sections are outside the desired values, the article may not provide desired levels of comfort. Additionally, the pad sections may not provide desired levels of protection and coverage.

A further feature of the first pad section 26 can include a first pad thickness 58. In particular arrangements, the first pad thickness 58 can be at least a minimum of about 1.8 mm. The first pad thickness can alternatively be at least about 2 mm, and can optionally be at least about 2.4 mm to provide improved performance. Additionally, the thickness of the first pad section can be up to a maximum of about 4.5 mm, or more. The first pad thickness can alternatively be up to about 4.2 mm, and can optionally be up to about 4 mm to provide improved effectiveness. Such arrangements can, for example, be employed in articles that are typically referred to as "ultrathin" pads.

In other arrangements, the first pad thickness 58 can be at least a minimum of about 0.8 mm. The first pad thickness can alternatively be at least about 1 mm, and can optionally be at least about 2 mm to provide improved performance. Additionally, the thickness 58 of the first pad section can be up to a maximum of about 4 mm, or more. The first pad thickness can alternatively be up to about 3.7 mm, and can optionally be up to about 3.5 mm to provide improved effectiveness. Such arrangements can, for example, be employed in articles that are typically referred to as "pantiliners".

Similarly, the second pad section 28 can also have a selected, second pad thickness 60. In particular arrangements, the second pad thickness can be at least a minimum of about 1.8 mm. The second pad thickness can alternatively be at least about 2 mm, and can optionally be at least about 2.4 mm to provide improved performance. Additionally, the thickness of the second pad section can be up to a maximum of about 4.5 mm, or more. The second pad thickness can alternatively be up to about 4.2 mm, and can optionally be up to about 4 mm to provide improved effectiveness. Such arrangements can, for example, be employed in articles that are typically referred to as "ultrathin" pads.

In other arrangements, the second pad thickness 60 can be at least a minimum of about 0.8 mm. The second pad thickness can alternatively be at least about 1 mm, and can optionally be at least about 2 mm to provide improved performance. Additionally, the thickness 60 of the second pad section can be up to a maximum of about 4 mm, or more. The second pad thickness can alternatively be up to about 3.7 mm, and can optionally be up to about 3.5 mm to provide improved effectiveness. Such arrangements can, for example, be employed in articles that are typically referred to as "pantiliners".

If the thicknesses of the first and/or second pad sections are outside of the desired values, the article may be excessively bulky or may have insufficient strength. The article may also have insufficient strength or integrity.

With reference to FIGS. 1 and 2, the first pad section 26 can have a first longitudinal length 48. In particular aspects, the first longitudinal length can be at least a minimum of about 12 cm. The first longitudinal length can alternatively be at least about 13 cm, and can optionally be at least about 14 cm to provide improved performance. In other aspects, the first longitudinal length can be up to a maximum of about 26 cm, or more. The first longitudinal length can alternatively be up to about 21 cm, and can optionally be up to about 17 cm to provide improved effectiveness.

Similarly, the second pad section 28 can have a second longitudinal length 50. In particular aspects second longitudinal length can be at least a minimum of about 4 cm. The second longitudinal length can alternatively be at least about 5 cm, and can optionally be at least about 6 cm to provide improved performance. In other aspects, the second longitudinal length 50 can be up to a maximum of about 12 cm, or more. The second longitudinal length can alternatively be up to about 10 cm, and can optionally be up to about 7 cm to provide improved effectiveness.

If the longitudinal lengths of the first and/or second pad sections are outside the desired values, the article may not provide desired levels of comfort or the pad sections may not provide desired levels of coverage and protection.

With reference to FIGS. 1 and 2, the first pad section 26 can overlap the second pad section 28 by a selected overlap length 52, and the overlap length can provide a selected overlap percentage. In particular aspects, the overlap percentage can be at least a minimum of about 3%, as determined with respect to the longitudinal length of the longer first pad section. The overlap percentage can alternatively be at least about 15%, and can optionally be at least about 20% to provide improved performance. In other aspects, the overlap percentage can be up to a maximum of about 60%, or more. The overlap percentage can alternatively be up to about 50%, and can optionally be up to about 40% to provide improved effectiveness. In a desired arrangement the overlap percentage can be up to about 25%.

If the overlap percentage is outside the desired values, it may be excessively difficult to separate the first and second pad sections, the article may not provide desired levels of coverage and protection or the article may be excessively bulky.

The overlap percentage can be determined by employing the following formula:

Overlap %=100*(length of overlap)÷(length of longer, first pad)

Where the first garment-attachment mechanism 36 includes a garment adhesive, the second body-side cover 38 can be releasably removable from the first garment-adhesive while allowing the first garment-adhesive to operatively attach to an appointed undergarment. This ability to release may, for example, be assisted by providing an embossing pattern on the second cover 38 to enhance its ability to release from the garment adhesive. Conventional garment adhesives which are well known in the art can be suitably employed, and are available from commercial vendors.

In optional arrangements, the article 20 and the pad sections 26 and/or 28 may include additional components or component layers, as desired. In another feature, the article may include any desired pattern of embossments formed into at least the bodyside surface of either or both of the pad sections. The embossing can deform the bodyside of the cover and can deform selected portions of the topsheet and absorbent body members to provide operative channel regions that can help block, direct or otherwise control a desired movement of liquids along the bodyside surface of the article. The embossing can also provide an aesthetic benefit to the consumer, and a visual cue regarding fit and leakage protection. In particular arrangements, the embossments can be positioned generally adjacent the perimeter edges of the absorbent body members. In other aspects, the embossments can be configured to provide a regular or irregular pattern having one or more channels which are distributed in a symmetrical or asymmetrical array, as desired.

In the construction of the article 20 and the individual pad sections 26 and 28, the various components may be assembled and held together with any operative securement mechanism or system. For example, the desired attachments or securements can include adhesive bonds, cohesive bonds, thermal bonds, ultrasonic bonds, pins, snaps, staples, rivets, stitches, welds, zippers, or the like, as well as combinations thereof.

Those skilled in the art will recognize that the present invention is capable of many modifications and variations without departing from the scope thereof. Accordingly, the detailed description and examples set forth above are meant to be illustrative only and are not intended to limit, in any manner, the scope of the invention as set forth in the appended claims.

The invention claimed is:

1. An absorbent article having a longitudinal direction and a lateral cross-direction, said article comprising a first pad section and a relatively smaller second pad section which is operatively joined to the first pad section;
    said first pad section including a first topsheet, a first backsheet, a first absorbent body located between said first topsheet and said first backsheet, and a first region of a first garment-attachment mechanism located on a garment-side surface of said first backsheet;
    said second pad section including a second topsheet, a second backsheet, a second absorbent body located between said second topsheet and said second backsheet, and a second region of a second garment-attachment mechanism located on a garment-side surface of said second backsheet;
wherein
    said first pad section has a first longitudinal length and overlaps at least a portion of a bodyside surface of said second pad section;
    at least a portion of said first backsheet is configured to overlap at least an adjacent portion of a bodyside of said second topsheet;
    at least a portion of said first region of the first garment-attachment mechanism operatively attaches said first pad section to said second pad section;
    said first pad section overlaps said second pad section by an overlap length; said overlap length provides an overlap percentage defined by the following equation Overlap %=100%*(overlap length)÷(first longitudinal length)

which is not more than about 60%; and
said absorbent article has a total absorbent capacity, and said first absorbent body has an absorbent capacity which is at least about 55% of said total absorbent capacity wherein said absorbent article is a feminine care article; and
wherein said second pad section can be selectively separated from said first pad section, and said second pad section can be independently employed as a second reduced-size feminine care article.

2. An absorbent article as recited in claim 1 wherein said first garment-attachment mechanism operatively attaches said first backsheet to said second topsheet.

3. An absorbent article as recited in claim 1 wherein said first garment-attachment mechanism includes a first garment-adhesive; and said second garment-attachment mechanism includes a second garment-adhesive.

4. An absorbent article as recited in claim 1 wherein
    at least a portion of said first pad section extends longitudinally beyond a terminal end edge of said second pad section; and
    at least a portion of said second pad section extends longitudinally beyond a terminal end edge of said first pad section.

5. An absorbent article as recited in claim 1, wherein said absorbent article has a total absorbent capacity which is at least about 5 grams of menses simulant.

6. An absorbent article as recited in claim 1, wherein said absorbent article has a total absorbent capacity, and said first absorbent body has an absorbent capacity which is between about 60% and 90% of said total absorbent capacity.

7. An absorbent article as recited in claim 1 wherein said first pad section can be selectively separated from said second pad section, and said first pad section can be independently employed as a first reduced-size feminine care article.

8. An absorbent article as recited in claim 7 wherein said first pad section has area size which is not more than about 120 cm$^2$.

9. An absorbent article as recited in claim 7 wherein said first pad section has first pad thickness which is not more than about 4.5 mm.

10. An absorbent article as recited in claim 7, wherein said first pad section has a first longitudinal length which is up to a maximum of about 26 cm.

11. An absorbent article as recited in claim 1 wherein said second pad section has area size which is not more than about 12 cm$^2$.

12. An absorbent article as recited in claim 1 wherein said second pad section has second pad thickness which is not more than about 4.5 mm.

13. An absorbent article as recited in claim 1, wherein said second pad section has a second longitudinal length which is up to a maximum of about 12 cm.

14. An absorbent article as recited in claim 1 wherein said first pad section has a tapered shape which is configured to provide an operative absorbent liner for a thong undergarment.

15. An absorbent article as recited in claim 1, wherein
said first garment-attachment mechanism includes a first adhesive; and
said second bodyside topsheet is releasably removable from said first garment-adhesive while allowing said first garment-adhesive to operatively attach to an appointed undergarment.

16. An absorbent article as recited in claim 1, wherein said overlap percentage is at least about 3% and is not more than about 50%.

17. An absorbent article as recited in claim 1, wherein said overlap percentage is at least about 15% and is not more than about 40%.

18. An absorbent article as recited in claim 1, wherein the first pad section has a narrowest cross-direction width and the second pad section has a second narrowest cross-direction width, wherein the first narrowest, cross-direction width is smaller than or equal to the second narrowest cross-direction width.

19. An absorbent article as recited in claim 1, wherein the first pad section has a largest cross-direction width and the second pad section has a second largest cross-direction width, wherein the first largest cross-direction width is approximately equal to the second largest cross-direction width.

20. An absorbent article having a longitudinal direction and a lateral cross-direction, said article comprising a first pad section and a relatively smaller second pad section which is operatively joined to the first pad section;
said first pad section including a first topsheet, a first backsheet, a first absorbent body located between said first topsheet and said first backsheet, and a first region of a first garment-attachment mechanism located on a garment-side surface of said first backsheet;
said second pad section including a second topsheet, a second backsheet, a second absorbent body located between said second topsheet and said second backsheet, and a second region of a second garment-attachment mechanism located on a garment-side surface of said second backsheet;
wherein
said first pad section has a first longitudinal length and overlaps at least a portion of said second pad section;
at least a portion of the first pad section extends longitudinally beyond a terminal end edge of the second pad section;
at least a portion of the second pad section extends longitudinally beyond a terminal end edge of the first pad section;
said first pad section overlaps said second pad section by an overlap length; said overlap length provides an overlap percentage defined by the following equation Overlap %=100%*(overlap length)÷(first longitudinal length)

which is not more than about 60%; and
said absorbent article has a total absorbent capacity, and said first absorbent body has an absorbent capacity which is at least about 55% of said total absorbent capacity wherein the first pad section has a largest cross-direction width and the second pad second section has a second largest cross-direction width, wherein the first largest cross-direction width is approximately equal to the second largest cross-direction width.

21. An absorbent article as recited in claim 20, wherein said first pad section overlaps onto a body-side surface of said second pad section.

22. An absorbent article as recited in claim 20, wherein said overlap percentage is at least about 15% and is not more than about 40%.

23. An absorbent article as recited in claim 20, wherein the first pad section has a narrowest cross-direction width and the second pad section has a second narrowest cross-direction width, wherein the first narrowest cross-direction width is smaller than or equal to the second narrowest cross-direction width.

* * * * *